United States Patent
Pomato et al.

(10) Patent No.: US 8,343,508 B2
(45) Date of Patent: Jan. 1, 2013

(54) BOTULINUM ANTITOXIN COMPOSITIONS AND METHODS

(75) Inventors: Nicholas Pomato, Frederick, MD (US); Martin V. Haspel, Seneca, MD (US); Janet H. Ransom, North Potomac, MD (US)

(73) Assignee: Intracel Holdings LLC, Frederick, MD (US)

( * ) Notice: Subject to any disclaimer, the term of this patent is extended or adjusted under 35 U.S.C. 154(b) by 0 days.

(21) Appl. No.: 12/636,315

(22) Filed: Dec. 11, 2009

(65) Prior Publication Data

US 2010/0150934 A1 Jun. 17, 2010

Related U.S. Application Data

(63) Continuation of application No. 10/848,364, filed on May 19, 2004, now abandoned, which is a continuation of application No. 10/644,793, filed on Aug. 21, 2003, now abandoned.

(51) Int. Cl.
*A61K 39/08* (2006.01)
*A61K 45/00* (2006.01)
*A61K 39/00* (2006.01)
*A61K 39/02* (2006.01)

(52) U.S. Cl. ............... 424/239.1; 424/278.1; 424/184.1; 424/236.1; 424/247.1

(58) Field of Classification Search .................. None
See application file for complete search history.

(56) References Cited

U.S. PATENT DOCUMENTS 5,807,741 A * 9/1998 Brown et al. ................. 435/340
2006/0018877 A1 * 1/2006 Mikszta et al. .............. 424/93.1

OTHER PUBLICATIONS

Walsh, Proteins Biochemistry and Biotechnology (text book), 2002; pp. 131, 134-137, 252-255 and 258. (16 pages total).*
Kozaki et al. (Infection and Immunity, Dec. 1977; 18(3): 761-766).*
Middlebrook et al., Current Topics in Microbiology and Immunology, 1995; 195: 89-122.*
Walsh, Proteins Biochemistry and Biotechnology (text book), 2002; pp. 131, 134-137, 252-255 and 258.*
Billiau et al., Journal of Leukocyte Biology, 2001; 70: 849-860.*
Harris et al., Micron, 1999; 30: 597-623.*

* cited by examiner

*Primary Examiner* — Vanessa L. Ford
*Assistant Examiner* — Lakia Tongue
(74) *Attorney, Agent, or Firm* — Dickstein Shapiro LLP

(57) ABSTRACT

This invention provides *botulinum* antitoxin compositions and methods of production, and methods of treating animals and humans prophylactically and also those suspected of having contacted botulism toxin. The *botulinum* antitoxin is prepared by inoculating an animal with a monovalent *botulinum* toxoid and toxin. The animal's plasma is collected and purified at a high pH by affinity chromatography. The resulting monovalent immunoglobulins are de-speciated by digestion with pepsin. Monovalent antitoxins for all seven *botulinum* serotypes are then combined to produce a high titered heptavalent *botulinum* antitoxin composition.

34 Claims, No Drawings

BOTULINUM ANTITOXIN COMPOSITIONS AND METHODS

This application is a continuation of application Ser. No. 10/848,364 filed on May 19, 2004 now abandoned which is a continuation of Ser. No. 10/644,793, filed on Aug. 21, 2003, now abandoned the entire disclosures of which are hereby incorporated by reference.

GOVERNMENT RIGHTS

The United States Government has certain rights in this invention pursuant to Contract No. DAMD 17-93-C-3132 between the Department of the Defense and Intracel Resources LLC.

FIELD OF THE INVENTION

The present invention is directed to *botulinum* antitoxin compositions and methods for their production and use. More particularly, the present invention provides in one embodiment large scale purification and de-speciation procedures and the controlled combination of different antitoxins to produce consistently high titered heptavalent antitoxin compositions.

BACKGROUND OF THE INVENTION

*Clostridium botulinum* produces one of the most toxic substances known to man and presents a serious threat to human safety. The *botulinum* toxin is so potent that a lethal dose for an adult may be as low as 1 µg. *Botulinum* toxin works by blocking conduction at the neuromuscular junction and preventing the release of acetylcholine, which results in severe flaccid paralysis. Eventually, the cholinergic autonomic blockade leads to respiratory collapse and death.

There are seven different serotypes of *C. botulinum* and consequently seven immunologically distinct toxins. These seven toxins are identified as BoNT-A through BoNT-G and have different characteristics. BoNT-A is the most prevalent in nature and it, along with BoNT-B, is implicated in most cases of wound botulism and infant botulism. BoNT-F produces a toxin that is 60 times stronger than the toxin produced by BoNT-B.

Though botulism infections have traditionally been food-borne, wound induced, or infant related, several countries are reported to have developed *botulinum* toxin compositions for use as potential biological weapons. Furthermore, the prevalence and lethality of *botulinum* toxin give rise to potential risks by terrorist organizations. There are several unique challenges posed by such risks. First, unlike naturally occurring botulism, a biological weapon may contain a combination of the different toxins in specific amounts, so as to cause the most damage. Second, large segments of the population may become infected simultaneously. Thus, there exists a need to develop large scale *botulinum* antitoxin compositions directed to all of the *botulinum* toxins, not just those toxins most prevalent in nature.

Previous methods of manufacturing *botulinum* antitoxin compositions have produced unreliable results. Typically, a single animal was immunized with all seven *botulinum* toxins. This produced a product with variations in the levels of different *botulinum* titers. In particular, it was difficult to obtain a high titer response to *botulinum* toxins F and G through such immunization. Furthermore, previous immunization methods used alum-precipitated toxoids, which resulted in low titered antitoxins inadequate to meet the requirements of a clinically useful antitoxin produced in sufficient quantities for treating large numbers of patients.

For example, in 1991 the United States military tested a heptavalent *botulinum* antitoxin developed from horse serum. See U.S. Pat. No. 5,719,267. For this antitoxin, the military injected a single horse with toxoids for all seven *botulinum* toxins and used the resulting antitoxins. Specifically, the antitoxins were comprised of the F(ab')$_2$ portion of the antibody molecule. However, this method of production was unreliable because there was no control over the various concentrations of the different antitoxins produced in the horse.

Furthermore, previous methods were not suitable for large scale production of *botulinum* antitoxin. For example, previous methods used Cohn fractionation for isolating *botulinum* antibodies from plasma. The use of Cohn fractionation, however, is less effective in large scale manufacturing because large volumes of plasma must be subjected to centrifugation and the method produces antibodies with relatively low purity.

Additionally, previous methods of de-speciating equine *botulinum* antibodies were not particularly effective, and were quite ineffective for producing *botulinum* antitoxin on a large scale basis. Such methods of digestion included the use of pepsin at 37° C. over a period of 4 hours, which often resulted in incomplete digestion. Thus, long incubation periods of approximately 18-24 hours were required to achieve complete digestion under physiological conditions. To increase the rate of incubation and decrease incubation time, the incubation temperature may be increased to 70° C. However, that temperature is not compatible with achieving an active antitoxin preparation. Alternatively, a preliminary incubation of IgG at low pH, such as pH 2.8, also facilitates enzymatic digestion. However, utilizing such a low pH causes aggregation and precipitation of equine IgG.

What is needed is a reliable method of manufacturing *botulinum* antitoxin, preferably on a large scale basis, to produce a high titered antitoxin composition. The method of manufacture should allow for the combination of different *botulinum* antitoxins so that the final composition may contain high titers to all seven of the *botulinum* toxins.

BRIEF SUMMARY OF THE INVENTION

The present invention overcomes the problems of the prior art and provides *C. botulinum* antitoxin compositions and methods for the large scale production, purification, and manufacture of *C. botulinum* antitoxin. The invention provides a high titer *botulinum* antitoxin. Preferably, the *botulinum* antitoxin composition has a protein concentration of about 30-70 mg/ml; a pH of about 6-8; and is about 95% pure. The purity represents the quantity of fragmented equine antibody present relative to other materials in the composition as determined by size exclusion high performance liquid chromatography and/or sodium dodecyl sulfate capillary electrophoresis. Furthermore, the invention provides methods of prophylaxis and treatment by administering an effective amount of *botulinum* antitoxin compositions which are preferably produced by the method of manufacture described herein.

In one embodiment, the invention provides for the manufacture of a heptavalent *botulinum* antitoxin composition derived from horses. Several horses are each inoculated with a single *botulinum* serotype toxoid so as to produce a monovalent antitoxin reaction in each horse. The toxoids may be produced by inactivating each of the *botulinum* toxins through any suitable means, such as by the use of formalin. Both the toxoids and toxins are commercially available from, for example, METAbiologics, Inc., Madison, Wis. The horses receive several injections of toxoid, preferably intradermally and mixed with an adjuvant, over several weeks to stimulate the monovalent antitoxin response. To achieve high antibody titer levels, the horses may be further immunized with purified toxin. The toxin may be injected as a native protein but more preferably is conjugated to clinical grade, purified native Keyhole limpet hemocyanin ("KLH"). After immunization with toxin, plasma is collected from the horses using plasmapharesis techniques. The pooled plasma is then clarified, such as by passage through a series of Millipore cartridge assembly filters.

The clarified plasma is then purified by affinity chromatography using, for example, affinity resins such as Protein G-Sepharose™ FastFlow (available from Amersham Biosciences, Piscataway, N.J.) for binding and elution. Elution of purified IgG is accomplished by using buffer at a high pH, preferably pH between about 10-12, and most preferably at pH 11. Purified immunoglobulins may then be pumped into a process vessel and maintained at a temperature of about 2-8° C.

The purified immunoglobulins are then digested to de-speciate the immunoglobulins, i.e., to remove material that may cause an unwanted immunogenic response in humans. The immunoglobulins may be adjusted to a pH between about 2.5 to 6.0, and most preferably about pH 4.5. The temperature may be raised to about 22-24° C. A 30% (w/v) pepsin solution may be made in 50 mM sodium acetate, at about pH 4.5. The pepsin may be obtained from CalBiochem. The pepsin solution may be added to the vessel to achieve an enzyme to substrate ratio of between about 1:5 to 1:50, and preferably of about 1:25, and then the temperature is preferably raised to between about 35 to 65° C., and most preferably about 58° C. This digestion process produces $F(ab')_2$ and Fab or Fab' fragments from each horse that have monovalent antitoxin activity depending on the specific serotype toxin injected in each horse.

The resulting digested immunoglobulins may then be concentrated, diafiltered, and clarified. The $F(ab')_2$ and Fab fragments are preferably further purified such as by anion exchange column and submitted for final bulk product filtration. The resulting monovalent antitoxin product may then be stored until further processing.

The monovalent antitoxins for all seven *botulinum* toxins are then combined based on each serotype's potency to create a heptavalent product. The various serotypes may be mixed in any amounts, and preferably based on the following potencies: antitoxin for serotypes A, B, C, E, F>4,000 International Units (I.U.) per dose and for serotypes D and G>500 I.U. per dose. If desired, the resulting heptavalent antitoxin composition may be supplemented with monoclonal antibodies directed against specific neurotoxins, such as BoNT-F and BoNT-G. The monoclonal antibodies may be produced, for example, from mouse myeloma and equine lymphocyte heterohybridomas. A cryoprotectant excipient may be added and the material then filtered and lyophilized.

The resulting de-speciated heptavalent antitoxin composition preferably has a protein concentration of about 30-70 mg/ml; a pH of about 6-8; and preferably is at least about 95% pure. These and other advantages and features of the invention will be more readily understood from the following detailed description.

DETAILED DESCRIPTION OF THE INVENTION

Reference will now be made in detail to the presently preferred embodiments of the invention, which, together with the following examples, serve to explain the principles of the invention. These embodiments are described in sufficient detail to enable those skilled in the art to practice the invention, and it is to be understood that other embodiments may be utilized, and that structural, biological, and chemical changes may be made without departing from the spirit and scope of the present invention.

The present invention provides compositions and methods for the production and manufacture of *botulinum* antitoxin compositions. The antitoxin compositions are derived from animals, preferably horses. An individual animal is inoculated with a monovalent toxoid so that each animal produces antitoxin to one *botulinum* serotype. The antitoxin obtained and purified from each individual animal is then combined in a controlled manner, as described above, based on each serotype's potency, to create a uniformly high titered polyvalent *botulinum* antitoxin composition. The method is particularly well-suited for operation at large scale, e.g., processing of hundreds of liters of plasma. A preferred preparation may start with 100 liters of the monovalent antitoxin. This method of producing *botulinum* antitoxin compositions is advantageous over previously known methods, which involved immunizing one animal with all seven *botulinum* serotypes. Given the differing immunogenicity of the seven *botulinum* toxins, a uniformly high titered preparation was not obtained with the previous methods.

Immunization and Plasmapharesis. Several animals, preferably horses, are each inoculated with a different monovalent *botulinum* toxoid so as to produce a different monovalent *botulinum* antitoxin in each horse. The toxoids may be made by inactivating the *botulinum* toxins with formalin. However, other methods for inactivating toxins, such as using cross-linking reagents like glutaraldehyde, extreme pH, or elevated temperatures, may also be used. Each horse receives injections of toxoid sufficient to establish a high titer antitoxin response. Preferably, titers of >500 I.U. per mL for antitoxins to serotypes A, B, C, D, and E; and titers of >200 I.U. per mL for serotypes F and G are obtained. Preferably, each horse receives a set of injections of between 5 and 30 injections, and preferably 20 injections, of toxoid intradermally on one or more separate occasions over the course of 2-8 weeks. The sets of injections are given preferably at 14 day intervals until the antitoxin titer reaches a level suitable for protecting the horse from subsequent toxin injections. The toxoid may be mixed with adjuvant, such as Freund's Adjuvant or RIBI's adjuvant system (MPL+TDM=CWS emulsion), available from RIBI ImmunoChem Research Inc., Hamilton, Mont., before injection.

The first set of injections may contain between 1-5 mg of toxoid mixed with Complete Freund's Adjuvant. Preferably, the amount of toxoid is 1-3 mg, and more preferably about 2 mg. Between 10-21 days later, each horse may receive a second set of injections mixed with Incomplete Freund's Adjuvant. Preferably, the time after the first set of injections is 14 days and the amount of toxoid is about 0.1 to 1.0 mg, and more preferably about 0.5 mg. Typically, injections are given intradermally using multiple sites at approximately 0.05 to 0.15 mL per site, and preferably 0.1 mL per site. The preferred site for the injections is a rectangular area measuring approximately 24×8 inches on the horse's back, just lateral to the midline, posterior to the withers, and anterior to the pelvis. One side may be used for the first set of injections, and the other side used for the second set of injections.

Approximately 14 days after the second set of injections, the antitoxin titers of the horses are tested, preferably using a mouse neutralization assay, to determine if an immune response sufficient to neutralize subsequent injection of toxin has been evoked. If the immune response is not sufficient, subsequent priming doses of toxoid may be performed until the immune response is determined to be sufficient. These priming doses may also be mixed with an adjuvant, such as RIBI's adjuvant system.

Once the horses' antitoxin titers are sufficient, the horses may be immunized with a booster injection of purified toxin. This booster injection may comprise an intradermal injection between 50-200 μg of the *botulinum* toxin specific for that horse, and preferably about 100 μg. In order to achieve a maximized immune response, the toxin may be conjugated to clinical grade, purified, native KLH. The KLH should be derived from a controlled source of material (not from limpet randomly harvested from the ocean) and should be purified to remove potential non-KLH contaminants. In order to achieve a maximum immune response, the KLH should be in its native form consisting of at least 50% of the dodecamer form of the glycoprotein. Other forms of KLH may be used but can evoke less of an immune response. The KLH should have low endotoxin levels and should be immunoreactive. The toxin may be conjugated by a variety of methods including periodate oxidation followed by Schiff base formation which is then stabilized by mild reduction, homobifunctional cross linkers and heterobifunctional cross linkers (as described in the catalog and handbook from Pierce, Rockford, Ill., herein incorporated by reference in its entirety). The toxin or more preferably, the conjugated toxin, may be admixed with an adjuvant such as RIBI's adjuvant system. The antitoxin plasma is then obtained from the horses using plasmapheresis or any suitable technique for obtaining animal plasma without adversely affecting the antitoxin.

Purification of Immunoglobulins. The plasma is then preferably clarified and purified to isolate the immunoglobulins. The pooled plasma is first tested for antitoxin activity by any suitable means, most preferably by using a mouse neutralization assay, and then clarified. The plasma may be clarified by passage through a series of filters, such as Millipore cartridge assembly filters available from Millipore Corp., Billerica, Mass. Preferably, the series of filters includes 2.0μ, 1.2μ, 0.5μ, and 0.22μ. After the plasma is clarified, it may be collected in a jacketed vessel of about 110 L or more and maintained at a temperature of about 2-8° C. so that it can be purified.

Purification of the plasma is then performed by affinity chromatography. As equine IgG binds poorly to protein A, we have developed a method of using Protein G for binding and elution. The column is preferably washed several times with Water for Injection, 10 mM carbonate/bicarbonate buffer (pH 11), and phosphate buffer solution ("PBS") (pH 7.5), or other suitable buffers, for equilibration. After equilibration, samples may be collected for endotoxin, pH, and conductivity assays. Preferable specifications for such assays are as follows: endotoxin >1 Eu/mL; pH 7-7.4; and conductivity 17-21 mS/cm. If the assays do not meet the specifications, the column may be re-equilibrated until the desired specifications are met.

To process a batch of 100 L of plasma, clarified plasma may be loaded onto the column in volumes up to 27 L and washed with 60 L of PBS. Though immunoglobulins are typically eluted from Protein G at a low pH, this causes precipitation and aggregation of the IgG and results in low yields. We have discovered that elution from Protein G at a high pH produces high yield. Preferably, the pH should be between pH about 10-12. Most preferably, the pH is about pH 11. Elution may be accomplished with 120 L of 10 mM carbonate/bicarbonate buffer. Protein G purified material is then pumped into a jacketed process vessel maintained at a temperature of about 2-8° C. and a protein concentration of ≧3.0 mg/ml. The column is washed with PBS to re-equilibrate between sample applications. To complete a 100 L batch of plasma, 3-4 applications may typically be performed to yield about 80% or more recovery of >95% pure immunoglobulin fractions containing both equine IgG and IgT having antitoxin activity.

De-Speciation of IgG. In order to create an antitoxin composition that can be administered to humans without causing an unwanted immunogenic response, the immunoglobulins are then de-speciated. De-speciation may be performed by digestion with pepsin. The digestion may be combined with moderate decreases of pH and increases of temperature to achieve digestion without sacrificing yield. The purified immunoglobulin is preferably diluted with 1 M sodium acetate to a concentration of 50 mM sodium acetate and a pH between about 2.5 and 6. Most preferably the pH is about pH 4.5. The temperature of the process vessel (e.g., 300 L) containing the purified material is raised to about 22-24° C. A pepsin solution is added to the vessel to achieve an enzyme substrate ratio of 1:25 and the temperature of the vessel is increased to between about 35-65° C., and more preferably to about 58° C. After approximately 2 hours, digestion may be stopped by adding 0.5 M dibasic sodium phosphate to raise the pH to about 6 or higher. The temperature is then returned to approximately 2-8° C.

This digestion process can eliminate all or virtually all intact IgG molecules, which may be highly immunogenic to humans. During the digestion process, the IgG is fragmented first to $F(ab')_2$ and then to Fab'. The antibody may be fragmented to contain an average of 60% $F(ab')_2$ and 40% Fab (or Fab') fragments having antitoxin activity. As intact quantities of IgG are digested, additional quantities of Fab' are produced.

Further Processing. The digested material may then be concentrated (e.g., to about 90-120 mg/ml) and diafiltered with PBS. Preferably, the concentrated material is diafiltered, such as by a CUF-Pellicon Cassette stainless steel ultrafiltration system with a low molecular weight cut-off of 30,000, to remove digestion buffers, pepsin, and any low molecular weight products. After filtration, the material is clarified, preferably using a 1.2μ filter.

Additionally, the $F(ab')_2$ and Fab fragments may be purified using an anion exchange column. The anion exchange column may contain, for example, 3.5 L of Q Sepharose™ Fast Flow chromatography resin, or any other suitable resin, having a bed height of about 29.5 cm. The column is equilibrated with PBS and the $F(ab')_2$ and Fab fragments are collected. The preferred elution buffer is 1.0 N sodium chloride in 40 nM sodium phosphate. PBS may be used for a final wash, after which the product may be submitted for final bulk product filtration. Final filtration may be performed using a Millipak 200, 0.22μ PVDG membrane filter, and the resulting monovalent antitoxin stored at a temperature of about 2-8° C.

Formulation of Polyvalent Antitoxin Composition. Monovalent antitoxins to different *botulinum* toxins may be combined to create a polyvalent antitoxin composition. In a preferred embodiment, monovalent antitoxins to all seven of the *botulinum* toxins are combined to create a heptavalent antitoxin composition. The monovalent antitoxins are preferably combined in a controlled manner based on each serotype's potency to achieve a heptavalent composition with a protein concentration of about 30-70 mg/ml and a final fill volume of 20-40 ml per vial. As necessary, the combined polyvalent composition may be diluted with a buffer, such as PBS, to meet the 30-70 mg/ml protein concentration specification. The ability to manufacture individual, monovalent antibodies according to the present invention provides the benefit of being able to produce a large quantity of highly controlled heptavalent antitoxin. For example, this process may start with 100 L of plasma containing approximately 3.5 kilograms of antibody, which can yield hundreds of grams of despeciated antitoxin. This process may also involve larger volumes of plasma, such as 1000 L of plasma.

Supplementing with Monoclonal Antibodies. To obtain relatively high titered antisera for *botulinum* toxins F and G, it may be desirable in some cases to supplement the heptavalent antitoxin composition with monoclonal antibodies directed against those toxins. Supplementation enhances the prospects of consistently obtaining a uniformly high titered antitoxin directed against all *botulinum* toxins.

In one method of creating the monoclonal antibodies, peripheral blood lymphocytes are isolated from whole blood samples obtained during the plasmaphoresis of horses immunized with *botulinum* neurotoxin (e.g., BoNT-F or BoNT-G) preferably using a gradient of appropriate buoyant density, such as Ficoll-Hypaque. Horse peripheral blood lymphocytes may be fused with a non-secretor mouse myeloma cell line that is thymidine kinase or HGPRT deficient. For example, a variant non-secretor mouse myeloma (NS-1) cell line may be used for the generation of the heterohybridomas. The mouse myeloma and peripheral blood lymphocytes may be mixed together under conditions of lymphocyte excess (such as a ratio of 10:1) and centrifuged together. The pelleted cells may be fused by electrofusion or chemical fusion techniques. In chemical fusion, a chemical such as 50% polyethylene glycol (PEG) of suitable molecular weight (e.g., 1000) is used. After the fusion process, the cells may be plated, under limited dilution conditions, in the presence of a suitable feeder cell layer (such as peritoneal exudates cells or irradiated macrophage-derived cell line) or conditioned medium antibodies. The heterohybridomas are selected with HAT (Hypoxanthine, Aminopterin, Thymidine) solution. As the chemotherapeutic drug aminopterin blocks de novo synthesis, the cells rely on scavenger pathways for synthesis of nucleotides. HGPRT deficient mutants, such as NS-1 cells, cannot synthesize DNA and therefore cannot grow in HAT medium. The necessary gene(s) for growth in HAT medium in the heterohybrids are supplied by the equine lymphocyte parent. The non-fused equine lymphocytes do not grow in the absence of lymphokines. The selection in HAT medium may continue for at least two weeks and then may be followed by growth in HT medium.

Once produced, the monoclonal antibodies are screened. Supernatants from IgG producing cells may be screened at the 96-well plate stage by testing their binding to the antigen used to immunize the donor horse and their inability to bind to irrelevant *botulinum* antigens. Preferably, cells from wells whose supernatant exhibit appropriate binding, i.e., only to the relevant antigen, may be cloned by suitable means, such as limiting dilution. Cells whose supernatant also binds to the non-immunizing antigen are discarded. Supernatants of the cloned cells may be screened first for IgG production and then binding to the *botulinum* toxin. If the assay results are acceptable, e.g., the cells produce over 5 µg/mL of IgG, the cells are re-cloned. Several rounds of cloning by limiting dilution or other means may be desirable to ensure stability.

Supernatants of the cloned cells may be selected based on antibody production, hybrid stability, and growth properties of the cell line. Supernatants may be first tested for neutralization of *botulinum* antitoxin with an in vitro assay, such as the phrenic nerve-hemidiaphragm assay described by Deshpande et al. (Deshpande, S. S., Sheriden, R. E. and Adler, M. A.; A Study of Zinc Dependent Metalloendopeptidase Inhibitors as Pharmacological Antagonists in *Botulinum* Neurotoxin Poisoning; Toxicon 33:551-7 (1995)). This assay has been reported as being more sensitive for the detection of toxin neutralization than the mouse survival assay.

In the phrenic nerve assay, phrenic nerve hemidiaphragm preparations are incubated at 37° C. in buffered saline solution under hyperoxic conditions (95% $O_2$/5% $CO_2$). *Botulinum* toxin of the appropriate serotype is incubated with or without the test antibody for 30 minutes at room temperature. Following this neutralization period, the neurotoxin antibody complex or neurotoxin saline control is added to the phrenic nerve hemidiaphragm preparation. Isometric twitch tension of the diaphragm is then measured, using a force displacement transducer, following stimulation of the phrenic nerve. The time to paralysis after a lag phase is linear with neurotoxin concentration. Elongation of time to paralysis is therefore a measure of the effectiveness of any antagonist (drug or antibody) to the toxin. This assay is of particular utility for the initial screening of Fab.

The neutralization observed in vitro may be confirmed in vivo in a mouse intraperitoneal ("IP") exposure and intravenous ("IV") treatment model. If desired, antibodies that neutralize *botulinum* neurotoxin in vitro may be tested for protection in two stages. For example, in the initial testing, mice in groups of 5 per serotype receive an IP injection of 25 $LD_{50}$ of a single toxin type. The negative control group receives an IV injection of saline approximately 45 minutes after toxin injection. Groups of 5 mice are injected with toxin-specific candidate antibody dosages of 2, 5, 10, and 25 mg/kg administered 45 minutes after injection of the toxin. Survival is assessed for 4 days, the length of time in which all mice should die from toxin exposure in a toxin potency or neutralization assay. The minimum concentration of each antibody needed to significantly protect the mice from mortality is used in the second phase of the testing.

The second phase of testing may use the minimum effective dose of antibody determined in the first phase. For example, each group may consist of 10 mice. In addition to the negative control and the 45 minute delay groups described above, a third group preferably is not treated with the antibody until the first sign of intoxication, which is defined as onset of a respiratory rate >160 respirations per minute. Intraperitoneal administration of 25 $LD_{50}$ of toxin typically results in a median time to death of mice from 2.8 to 10.4 hours depending upon the toxin type. Therefore, this assay can serve as a rigorous test of the antibody efficacy.

Once selected, the desired monoclonal antibodies may be added to the antitoxin composition to create a controlled high titer antitoxin that contains antitoxin for all seven toxins, including toxins F and G. In one embodiment, the antitoxins to serotypes A-E may be manufactured as fragmented polyclonal antibodies, and monoclonals for serotypes F and G may also be fragmented. At the final formulation steps when the heptavalent antitoxin mixture is made, all of the antibodies may be combined together to prepare a polyclonal heptavalent mixture, but the monoclonal antitoxins directed against serotypes F and G may supplement or replace their polyclonal counterparts.

Lyophilization. A suitable lyophilization technique is described below, in the event that a lyophilized antitoxin composition is desired. After the heptavalent composition is created, a cryoprotectant, such as lactose, may be added at a concentration of about 2% to 5%, and allowed to equilibrate and dissolve overnight. The material may then be filtered, preferably using a 0.22µ Duropore filter-housing unit, collected into a 200 L bag in stainless steel vessels, weighed, and filtered again with the 0.22µ filter. The filtered product may be dispensed into 100 ml glass vials, each with a target fill volume of about 23.94 ml. The stoppers to the vials may be seated in the vials in preparation for lyophilization.

The vials are then loaded into a lyophilizer. Within the lyophilizer, the shelf temperature may be adjusted to about −48° C. Thermocouples are placed into strategically located vials throughout the chamber to check the temperature. The temperature is held between about −45° C. and 48° C. for about 8 hours. After 8 hours, the condenser temperature may be adjusted to about −60° C., and the freeze dryer evacuated. A sterile nitrogen sweep is then initiated. Preferably, the nitrogen sweep is about 50-300 microns, and more preferably 100-200 microns. Once the chamber pressure reaches about 150 microns, the temperature of the shelves is typically adjusted to about −35° C. and held for 24 hours. After 24 hours, the shelf temperature is adjusted to about −30° C. and held for another 24 hours. After this 24 hours, the temperature may be increased to about −10° C. over a period of approximately 20 hours. The shelf temperature is then adjusted to about 0° C. and held there until all the thermocouples record a temperature of about −5° C. or higher.

At the end of the primary drying time, the shelf temperature in the lyophilizer is adjusted to about 20° C. and maximum vacuum pulled. After the shelf temperature is reached, the drying cycle is held for about 14 to 16 hours until all the thermocouples read about 17-23° C. for more than 8 hours. At this point, the drying cycle is ended and 5 bottles may be selected at random for moisture analysis. The remaining vials preferably undergo a final drying cycle until the moisture analysis is completed, and then the chamber is restored to atmospheric pressure with sterile nitrogen. The distance between the shelves is automatically decreased, which results in the vials being stoppered, and the shelf temperature is adjusted to 2-8° C. while the chamber is unloaded.

Release Testing. The preferred heptavalent antitoxin composition meets the release specifications summarized in Table 1.

TABLE 1

Quality Control Tests for the Release of Formulated Heptavalent De-speciated Equine *Botulinum* Antitoxin.

| TEST | SPECIFICATION |
| --- | --- |
| Physical: | |
| PH | 7.0-7.4 |
| Conductivity | 15.0-21.0 mS/cm |
| Protein Concentration | 30-70 mg/ml |
| Lactose Concentration | 5 ± 1% |
| Potency: | |
| Mouse Neutralization Assay: | |
| Serotypes A, B, C, E, F: | >4,000 IU/vial |
| Serotypes D, G: | >500 IU/vial |
| Purity: | |
| HPLC | >95% F(ab')$_2$ and Fab |
| CE | <5% Intact IgG, IgT |
| Integrity: | |
| HPLC | ≧60% F(ab')$_2$ |
| Identity: | ≦40% Fab' |
| SDS-PAGE | Mobility 1.0 ± .01 |
| Mouse Bioassay | Type-specific Neutralization |
| Safety: | |
| Endotoxin | <12 EU/ml |
| Sterility | No detectable microorganisms |

A particularly preferred process flow chart for obtaining antitoxin meeting the above specifications is set forth below.

IMMUNIZE HORSES

Immunize horses by multiple series of injections of one type of *Botulinum* toxoid admixed with adjuvant. Boost with 100 μg purified toxin 7-10 days before plasma collection.

⇓

COLLECT PLASMA

Collect 8-10 liters of blood from each immunized horse. Separate plasma from blood cells and return blood cells to horse. Freeze and store plasma.

⇓

CLARIFY PLASMA

Thaw and pool hyperimmune plasma (65-95 liters/batch) to a single toxin. Filter through a four stage system comprised of 2.0μ, 1.2μ/0.5 sandwich, 0.5μ/0.22μ sandwich and 0.22μ filters.

⇓

PURIFY IGG/IGT BY PROTEIN G CHROMATOGRAPHY

Chromotography (up to 27 L) on 30 L Protein G column, elute at high pH (pH 11). Perform 3-4 cycles/batch.

⇓

DE-SPECIATE IGG

Proteolytic cleavage of purified IgG by pepsin at pH 4.5 and 58° C. for 2.5 hours to produce F(ab')$_2$ and F(ab') fragments.

⇓

CONCENTRATION AND DIAFILTRATION

Concentrate to 90-100 mg/ml protein and diafilter (30,000 M.W. cutoff) with PBS to remove pepsin and small peptides.

⇓

CLARIFY F(AB)'$_2$/F(AB)' PRODUCT

Filter through sandwich 1.2μ/0.5μ membranes.

⇓

ANION EXCHANGE CHROMOTOGRAPHY

Collect non-bound F(ab)'$_2$/F(ab)' product from Q-FF anion exchange column to remove contaminants.

⇓

STERILE FILTRATION

Filter through 0.22µ absolute membrane. Store liquid sterile product at 2°-8° C. until formulation of heptavalent lot.

⇓

FORMULATE HEPTAVALENT ANTI-TOXIN

Combine each of the seven monovalent lots to achieve a heptavalent product with a potency per dose: anti-A (>4,000 IU), anti-B (>4,000 IU), anti-C (>4,000 IU), anti-D (>500 IU), anti-E (>4,000 IU), anti-F (>4,000 IU) and anti-G (>500)

⇓

FINAL FILL AND LYOPHILIZATION

Add lactose (final concentration 5% ± 1) as a cryoprotective excipient. The final product is filtered twice through 0.22µ filters and 23.94 mL is dispensed into each vial. The product is then lyophilized.

Application of the teachings of the present invention to a specific problem or environment is within the capabilities of one having ordinary skill in the art in light of the teachings contained herein. Illustrative examples of products and processes according to the present invention appear in the following examples.

Example 1

Immunization Regimen

In order to obtain high polyclonal antibody titers, we used a multi-step immunization procedure. Several horses were each immunized with a single *botulinum* serotype. First, the horses were immunized with the toxoid form, i.e., inactivated form of the toxin, of the specific toxin serotype to be used for that horse. The first inoculation contained 2 mg of toxoid in Complete Freund's Adjuvant injected intradermally using up to 30 sites at approximately 0.1 mL per site. After 14 days, the horses received a second inoculation of 0.5 mg toxoid in Incomplete Freund's Adjuvant injected intradermally at multiple sites at approximately 0.1 mL per site. After another 14 days, antitoxin titers were determined using a mouse neutralization assay and, if necessary, a subsequent priming dose of 0.5 mg of toxoid in RIBI's adjuvant system (MPL+TDM=CWS emulsion) was administered.

The injection site for the toxoid inoculations was a rectangular area measuring approximately 24×8 inches located on the horse's back, lateral to the midline, posterior to the withers, and anterior to the pelvis. One side of the horse was used for the first injection, and the other side was used for the second injection.

The horses were then immunized with toxin in order to obtain high antibody titers. For the toxin injections, approximately 100 µg of the toxin specific to that horse was admixed with the RIBI's adjuvant system and administered intradermally to the horse. The high titered antitoxin plasma was then obtained from the horses using conventional plasmapharesis techniques.

Using the method described above, over 10,000 liters of hyperimmune plasma were collected. The biological activity, i.e., toxin neutralization titers, of the obtained plasma are shown in Table 2.

TABLE 2

Summary of Collected Equine Plasma.

| Serotype | Total Liters | Average Antibody Titer (IU/ml) |
|---|---|---|
| A | 983 | 3,154 |
| B | 875 | 3,429 |
| C | 676 | 3,550 |
| D | 538 | 558 |
| E | 1,764 | 1,587 |
| F | 3,661 | 710 |
| G | 2,106 | 190 |
| Total Volume = 10,603 Liters | | |

In another embodiment, the toxin used in the immunizations is conjugated to KLH. For KLH conjugated toxin, the conjugate is made by treating 1 mg of KLH with 200 µL of 10 mM sodium periodate followed by removal of the excess periodate by dialysis. The oxidized KLH is then mixed with a 100 µg of azidobenzoyl hydrazide (Pierce, Rockford, Ill.) to create an arylazide activated protein. After removal of the excess azidobenzoyl hydrazide by dialysis, the activated KLH is mixed with 100 µg of the toxin. The conjugated toxin is admixed with the RIBI's adjuvant system and administered intradermally to the horse.

Example 2

Purification and De-Speciation of Equine *Botulinum* Antitoxins

Eighteen bags of frozen plasma, containing antitoxin to serotype B, were thawed, pooled together and clarified by filtration into a 110 L vessel. The total volume of plasma processed was 98 L. After clarification and rinsing of the filters with phosphate buffered solution ("PBS"), the volume of the sample was 103 L. This material was loaded onto 30 L protein G affinity columns in four cycles of 25.75 L per cycle. During each cycle, the antitoxin was eluted with 10 mM sodium bicarbonate/carbonate buffer in an average volume of 31.4 L. The total volume of antibody collected was 126.7 L with a protein concentration of 9.3 mg/mL. The antitoxin was collected into a 300 L vessel and diluted with 1M sodium acetate to a concentration of 50 mM sodium acetate, such that the pH was 4.5.

Pepsin was then added to the antibody solution at a concentration of 4% w/v and the temperature was adjusted to 58° C. After two hours, the digestion was halted by increasing the pH by adding 20 L 0.5 M sodium phosphate buffer and by lowering the temperature to 4° C. The antibody solution was diafiltered into PBS and the antibody was concentrated to at least 90 mg/mL. The concentrated antitoxin was clarified by filtration and then passed through a 2.5 L Q-Sepharose™ anion exchange column previously equilibrated in PBS. The antitoxin solution coming through the column was sterile filtered using a 0.22 µm filter. The final purified bulk antitoxin was tested for release in light of the specifications described above and stored until formulation into a heptavalent antitoxin product. The total quantity of antibody obtained from this procedure was 349 g with a yield of 24%.

Example 3

Formulation of the Heptavalent Antitoxin

Various monovalent batches of each of the seven antitoxin serotypes were processed as described above. The batches were pooled under aseptic conditions and based on the titers of the individual batches of antitoxin, the following volumes were combined: A-7.38 L; B-18.57 L; C-18.18 L; D4.86 L; E-3.11 L; F-24.82 L; and G-12.62 L. To this pool was added 120.79 L of phosphate buffered saline (PBS) and then 7.212 kilograms of solid lactose. The mixture was stirred for 16 hours at 2-8° C. The final lactose concentration was approximately 5%. The mixture was then filtered through a 0.22 micron filter and release tests described above were performed. This final purified bulk product was then vialed at approximately 23 mL (5-100 mL depending on the size of the lyophilization vial) per vial and lyophilized.

For lyophilization, the optimal cycle time is 96-110 hours (range could be 80-125 hours). The temperature of the trays when loading the vials into the lyophilizer should be about 48° C.±3° C. The vials were held in the lyophilizer at that temperature for a minimum of 8 hours, but can be held up to about 24 hours. At the end of this period, the condenser is adjusted to <−50° C. with an optimum temperature of −60 to −65° C. The chamber is then evacuated and the chamber pressure is adjusted to 100-200 microns by the addition of sterile, dry nitrogen (any inert gas can be used in place of the nitrogen). When the chamber reaches the proper pressure, the shelf temperature is adjusted to and held at −35° C.±3° C. for 24±1 hours. The shelf temperature is then adjusted to −30° C.±3° C. and held for an additional 24±1 hours. After this time, the temperature is ramped from −30° C. to −10° C.±3° C. at the rate of 1° C. per hour over the course of 20±0.5 hours. The shelf temperature is then adjusted to 0° C.±3° C. and held until all of the thermocouples inserted into the product are −5° C. or warmer. At the end of this primary drying cycle, adjust the shelf temperature to +20° C.±3° C. and pull the maximum vacuum. Before ending this terming drying cycle, all thermocouples should read +20° C.±3° C. for a minimum of eight hours (optimal is 8±1 hours). The chamber is then brought to atmospheric pressure using sterile, dry nitrogen. The vials are sealed by adjusting the distance between the shelves, and the shelf temperature is adjusted to +5° C.±3° C. and held at that temperature until the chamber is unloaded.

Example 4

Pre-Clinical In Vivo Studies of the Efficacy of a Heptavalent *Botulinum* Antitoxin Procedure. The efficacy of a heptavalent *botulinum* antitoxin was evaluated in a mouse intraperitoneal ("IP") exposure and intravenous ("IV") treatment model. Mice, in groups of 12 per serotype, were injected intraperitoneally with 25 $LD_{50}$ of a single toxin type. Three treatment groups for each toxin type were investigated. Group 1 (controls) received an IV injection of saline approximately 45 minutes after toxin injection. Group 2 received an IV injection of the heptavalent antitoxin 30 minutes after toxin injection. Group 3 received an IV injection of the heptavalent antitoxin at the first sign of intoxication, which was defined as onset of a respiratory rate of >160 respirations per minute. The dose of heptavalent antitoxin was the human equivalent dose on a weight basis, using a 70 Kg human as the standard. Survival was assessed for 4 days, the length of time in which all mice should die from toxin exposure in a toxin potency or neutralization assay. The results are summarized in Table 3. Intraperitoneal administration of 25 $LD_{50}$ of toxin typically results in a median time to death of mice from 2.8 to 10.4 hours depending on the toxin type. Therefore, this assay served as a rigorous test of antitoxin efficacy.

Results. As Table 3 demonstrates, mice that received antitoxin 30 minutes after receiving 25 $LD_{50}$ of toxin had an increased survival rate for all of the seven toxin types compared to mice in the other groups. If administration of antitoxin was delayed until the onset of clinical signs, there was not a significant survival benefit. However, in groups that received toxin serotypes E, F, and G, the antitoxin did effect a significant increase in time to death. Because death typically occurs shortly after onset of clinical signs, e.g., 1 to 4 hours, the demonstration of prolonged survival even when antitoxin was administered at this late stage of intoxication is highly significant.

TABLE 3

Efficacy of Heptavalent De-speciated *Botulinum* Antitoxin Administered Intravenously to Mice Following Intraperitoneal Administration of 25 $LD_{50}$ of Individual Botulinum Toxins (A-G).

| Serotype | Mean Time to Onset of Morbidity (hrs.)* | Median Time to Death of Controls (hrs.) | % Survival | | |
|---|---|---|---|---|---|
| | | | Group 1 (Control) | Group 2 (Antitoxin at 30 mins.) | Group 3 (Antitoxin at Onset) |
| A | 1.8 | 5.0 | 17 | 75 | 17 |
| B | 1.7 | 6.4 | 17 | 92 | 8 |
| C | 2.7 | 10.4 | 25 | 100 | 50 |
| D | 3.1 | 6.4 | 17 | 92 | 8 |
| E | 1.1 | 2.8 | 8 | 58 | 18 |
| F | 1.2 | 3.9 | 0 | 67 | 25 |
| G | 2.9 | 5.0 | 8 | 92 | 25 |

*Onset of increased respiratory rate (>160 respirations per minute)

Example 5

Pharmacokinetics and Safety Testing of a Heptavalent De-Speciated *Botulinum* Antitoxin Administered to Normal Human Volunteers Procedure. After passing a health screen, including skin tests to determine sensitivity to the heptavalent *botulinum* antitoxin, each of 25 volunteers was inoculated with a vialed dose of the heptavalent antitoxin product. Ten milliliters of blood were collected before administration of the product and then at each of these 15 time points following administration: 5 minutes, 15 minutes, 30 minutes, 1 hour, 2 hours, 4 hours, 8 hours, 20 hours, 44 hours, 79 hours, 7 days, 14 days, 21 days, 28 days, and 35 days. Each of the blood samples collected was processed for serum, which was frozen and held until the day 35 sample had been collected and processed.

Sixteen frozen serum samples were obtained from 15 of the 25 volunteers. Each aliquot was tested in a mouse neutralization assay. The *botulinum* neutralization assay in mice was conducted in the following manner. On day 0 for each assay, a serotype-specific antitoxin standard was diluted to a predetermined concentration. Four two-fold dilutions were made. An aliquot from each dilution was combined with an equal volume of *botulinum* toxin at a determined concentration, incubated at room temperature for 1 hour, and then inoculated intraperitoneally into mice.

Also on day 0 of each assay, the serum samples to be tested were thawed at room temperature. The selection of an initial dilution was based on the total volume available and on the expected protective titer, given the time point at which the sample was collected. Subsequent dilutions were either 4-fold or 16-fold and numbered either 2 or 4. The selection of a dilution factor and number of dilutions was based on the expected titer. As with the antitoxin standard, once the dilutions were completed, an aliquot of each serum sample was combined with an equal volume of *botulinum* toxin (the same used for the antitoxin standard). These preparations were vortexed, incubated at room temperature for 1 hour, and then inoculated intraperitoneally into mice. Each preparation was inoculated in a volume of 0.2 mL into 6-8 mice.

The mice were observed at least once post-inoculation on day 0, and then at least once per day for the next 4 days. Moribund mice, or those exhibiting signs of *botulinum* toxin poisoning, were euthanized upon discovery. At the end of each day, the Live/Dead tally was recorded. On day 4, a final observation was made and recorded, and all survivors were euthanized.

The data from each assay was analyzed by probit analysis, using SAS software. An antibody titer was calculated for each tested sample using assay-specific data ($LD_{50}$) in combination with previously established potency values for each antitoxin standard. In this way, the level of antibody in the serum of each of the 15 subjects was determined for each serotype at each time point.

Pharmacokinetic parameters were estimated using PKAnalyst Pharmacokinetic Data Analysis, Version 1.10 for Microsoft® Windows.® Serum titers from the majority of subjects were analyzed using a two compartment bolus input order output model. A few subjects had a better fit to a two compartment model with first order input, first order output. The serum clearance curves expressed in term of IU/mL were characterized by a biexponential equation (bolus input, first order output):

$$A_t = A_1 \cdot e^{-\alpha_1 t} + A_2 \cdot e^{-\alpha_2 t}$$

This equation was used to generate intercepts ($A_1$ and $A_2$) and clearance slopes ($\alpha 1$ and $\alpha 2$) or half lives ($T_{1/2}=0.693/\alpha$). Accordingly, the area under the curve AUC (IU×hr/mL) for each patient was obtained by simple integration method leading to:

$$AUC = A_1/\alpha_1 + A_2/\alpha_2$$

The clearance rate was determined from the infused dose and AUC:

$$CR = Dose/AUC$$

Half-life differences between serotypes were analyzed using a one way analysis of variance. Differences between pairs of groups were analyzed using the Tukey test.

Pharmacokinetic Analysis. Out of a possible 105 analyses, 83 (79%) generated curves that were analyzable using the methods described above. For the remaining subjects, the results for individual time points either fluctuated dramatically or showed no clear pattern of clearance. In many instances, time points that clearly did not fall on the curves had to be eliminated. Although the effective serum half-life of $F(ab')_2$ is similar to that of intact IgG, the effective half life of Fab is considerably shorter.

Using a one-way analysis of variance, there was no significant difference in the mean clearance half-life among the serotypes tested ($T_{1/2_\alpha}$–p=0.146, $T_{1/2_\beta}$–p=0.106). Additional analysis, using the Tukey test, indicated that there was also no difference ($\alpha<0.05$) between any pair of serotype clearance half-life means. The average of the half-life ($T_{1/2_\beta}$) for all serotypes is 21.3 hours.

Safety. It is clear from the data collected from the 53 subjects screened that the antitoxin composition caused no significant response in any of them, as compared to the expected response to the positive control material. Furthermore, the product was shown to be safe for use in humans, given the absence of any severe adverse experiences in any of the 25 subjects who received the entire infusion. Eight of the 25 subjects reported mild Adverse Experiences ("AE's"). The AE's reported were headache, dizziness, fatigue, thirst, nausea, and/or abdominal cramps. All AE's occurred within 1 day of administration. All 8 subjects reported full recovery from the reported conditions. Of the 21 subjects who returned for their 3-month follow-up health assessment, none reported any subsequent related AE's. The 4 remaining subjects withdrew voluntarily from the study either prior to completion of the blood sampling phase or subsequently. No AE's were reported for any of these 4 subjects.

All publications and patents mentioned in the above specification are herein incorporated by reference. The above description, tables, and examples are only illustrative of preferred embodiments which achieve the objects, features and advantages of the present invention. It is not intended that the present invention be limited to the illustrated embodiments. Any modification of the present invention which comes with the spirit and scope of the following claims is considered part of the present invention. For example, the affinity column may be changed from, for example, protein G to protein A. The pepsin used for digestion may be replaced by an enzyme with similar specificity. The anion exchange column used in the purification may have different functional groups, such as DEAE, QAE or PEI. The excipient used in the formulation can be a variety of excipients other than lactose, such as for example sucrose, maltose or fructose. Other sources of immune lymphocytes include lymph nodes, spleen and other lymphatic organs. Other species of myeloma cells may be used to immortalize the equine lymphocytes, and markers other than HGPRT and thymidine kinase may be used for the selection of heterohybridomas. Other methods of developing equine monoclonal antibody producing cell lines, such as phage display, are also considered to be within the spirit and scope of the invention.

What is claimed as new and desired to be protected by Letters Patent of the United States is:

1. A method for the manufacture of a *botulinum* antitoxin composition comprising:
    injecting an animal with a serotype of *botulinum* toxoid and the same single serotype of *botulinum* toxin to produce immunoglobulins and collecting plasma containing the immunoglobulins from the animal;
    purifying the immunoglobulins from the plasma by affinity chromatography;
    digesting the purified immunoglobulins by a proteolytic enzyme to obtain a monovalent *botulinum* antitoxin composition;
    combining a plurality of monovalent *botulinum* antitoxins for different *botulinum* toxins to create a polyvalent *botulinum* antitoxin composition; and
    supplementing the polyvalent *botulinum* antitoxin with *botulinum* monoclonal antibodies.

2. The method of claim 1, wherein the animal is a horse.

3. The method of claim 1, wherein the polyvalent *botulinum* antitoxin composition comprises antitoxin for seven different *botulinum* toxins.

4. The method of claim 3, wherein the antitoxins for serotypes A, B, C, E, and F have a potency >4,000 International Units and the antitoxins for serotypes D and G have a potency >500 International Units.

5. The method of claim 1, wherein the affinity chromatography uses immobilized Protein G.

6. The method of claim 1, wherein the monoclonal antibodies are produced from mouse myeloma cells and equine lymphocyte hybridomas.

7. The method of claim 1, wherein the monoclonal antibodies are directed against *botulinum* neurotoxins selected from the group consisting of neurotoxins F and G.

8. The method of claim 1, wherein the animal is injected intradermally with toxoid.

9. The method of claim 1, wherein the step of injecting the animal with a single serotype of *botulinum* toxin is performed after the step of injecting the animal with a single serotype of *botulinum* toxoid and before the step of collecting plasma containing immunoglobulins.

10. The method of claim 1, wherein at least one of the single serotype of *botulinum* toxoid and the same single serotype of *botulinum* toxin is injected together with an adjuvant.

11. The method of claim 1, wherein the animal is injected with a first injection of toxoid and a second injection of toxoid.

12. The method of claim 11, wherein the first injection comprises about 2 mg of toxoid.

13. The method of claim 11, wherein the first injection is injected at multiple sites at about 0.1 mL per site.

14. The method of claim 11, wherein the first injection further comprises Complete Freund's Adjuvant.

15. The method of claim 11, wherein the second injection is given about 14 days after the first injection.

16. The method of claim 11, wherein the second injection comprises about 0.5 mg of toxoid.

17. The method of claim 11, wherein the second injection further comprises Incomplete Freund's Adjuvant.

18. The method of claim 11, wherein the second injection is injected at multiple sites at approximately 0.1 mL per site.

19. The method of claim 11, wherein a priming dose of toxin is injected after the second injection of toxoid.

20. The method of claim 1, wherein the animal is injected with purified toxin about 7 to 10 days before the plasma is collected.

21. The method of claim 1, wherein the animal is injected with purified toxin conjugated to Keyhole limpet hemocyanin about 7 to 10 days before the plasma is collected.

22. The method of claim 1, further comprising clarifying the plasma through a filter after the plasma is collected.

23. The method of claim 22, wherein the filter comprises pore sizes selected from the group consisting of 2.0μ, 1.2μ, 0.5μ, and 0.22μ.

24. The method of claim 1, wherein the affinity chromatography is performed at a pH between about pH 10-12.

25. The method of claim 1, wherein the affinity chromatography is performed at about pH 11.

26. The method of claim 1, wherein pepsin is used to digest the purified immunoglobulins.

27. The method of claim 1, wherein the digesting is performed at a pH between about pH 2.5-6.0.

28. The method of claim 27, wherein the pH is about pH 4.5.

29. The method of claim 1, wherein the immunoglobulins are digested at a temperature of about 20-70° C.

30. The method of claim 29, wherein the temperature is about 58° C.

31. The method of claim 1, wherein the digested immunoglobulins are concentrated to about 90-100 mg/mL protein.

32. The method of claim 1, wherein the digested immunoglobulins are purified on an anion exchange column.

33. The method of claim 1, further comprising lyophilizing the antitoxin composition.

34. A method for the manufacture of a heptavalent *botulinum* antitoxin composition comprising: injecting a plurality of horses with *botulinum* toxoid mixed with an adjuvant wherein each individual horse is injected with a single serotype of *botulinum* toxoid; and wherein at least one horse is injected with each of serotypes A, B, C D, and E, injecting the horses with a single serotype of *botulinum* toxin after the injections of toxoid, wherein the serotype of *botulinum* toxin is the same as the serotype of *botulinum* toxoid; collecting from the horses plasma containing immunoglobulins and purifying the immunoglobulins from the plasma by affinity chromatography using immobilized Protein G, wherein the chromatography is performed at about pH 11; digesting the purified immunoglobulins with pepsin at a temperature of about 58° C. and a pH of about 4.5; filtering the digested immunoglobulins to obtain at least five monovalent *botulinum* antitoxins, wherein at least one of the at least five monovalent *botulinum* antitoxins is effective against *botulinum* serotype A; at least one of the at least five monovalent *botulinum* antitoxins is effective against *botulinum* serotype B; at least one of the at least five monovalent *botulinum* antitoxins is effective against *botulinum* serotype C; at least one of the at least five monovalent *botulinum* antitoxins is effective against *botulinum* serotype D; and at least one of the at least five monovalent *botulinum* antitoxins is effective against *botulinum* serotype E; combining the at least five monovalent *botulinum* antitoxins from the plurality of horses to create a polyvalent composition; supplementing the polyvalent composition with monoclonal antibodies directed against *botulinum* toxins F and G to produce a heptavalent composition; and lyophilizing the heptavalent composition.

* * * * *